US008280128B2

(12) United States Patent
Taxt et al.

(10) Patent No.: US 8,280,128 B2
(45) Date of Patent: Oct. 2, 2012

(54) METHOD OF GENERATING AN ENHANCED PERFUSION IMAGE

(75) Inventors: Torfinn Taxt, Bergen (NO); Renate Gruner, Bergen (NO)

(73) Assignee: Stiftelsen Universitetsforksning Bergen, Bergen (NO)

( * ) Notice: Subject to any disclaimer, the term of this patent is extended or adjusted under 35 U.S.C. 154(b) by 669 days.

(21) Appl. No.: 12/227,361

(22) PCT Filed: May 15, 2007

(86) PCT No.: PCT/GB2007/001802
§ 371 (c)(1),
(2), (4) Date: May 29, 2009

(87) PCT Pub. No.: WO2007/132242
PCT Pub. Date: Nov. 22, 2007

(65) Prior Publication Data
US 2009/0297008 A1 Dec. 3, 2009

(30) Foreign Application Priority Data
May 15, 2006 (GB) .................................. 0609610.1

(51) Int. Cl.
*G06K 9/00* (2006.01)
*G06K 9/64* (2006.01)
(52) U.S. Cl. ........ 382/128; 382/130; 382/131; 382/132; 382/279
(58) Field of Classification Search .................. 382/128, 382/130, 131, 132, 276, 279
See application file for complete search history.

(56) References Cited

U.S. PATENT DOCUMENTS
2007/0167731 A1* 7/2007 Taxt et al. ..................... 600/410

OTHER PUBLICATIONS

E. Henderson PhD, et al. "Simultaneous MRI Measurement of Blood Flow, Blood Volume, and Capillary Permeability in Mammary Tumors Using Two Different Contrast Agents", Journal of Magnetic Resonance, 2000, The British Library—"The world's knowledge" pp. 991-1003.
R. Gruner et al. "Iterative Blind Deconvolution in Magnetic Resonance Brain Perfusion Imaging" Magnetic Resonance in Medicine 55:805-815 (2006), pp. 805-815.
P. Totts et al. "Estimating Kinetic Parameters From Dynamic Contrast-Enhanced $T_1$-Weighted MRI of a Diffusable Tracer: Standardized Quantities and Symbols", Journal of Magnetic Resonance Imaging, 1999, The British Library—"The world's knowledge" pp. 223-232.
R. Gruner, et al. "Iterative blind deconvolution in magnetic resonance brain perfusion imaging", Magnetic Resonance in Medicine, Wiley, USA, Apr. 2006, vol. 55, No. 4, pp. 806-807.
E. Henderson, et al., "Simultaneous MRI measurement of blood flow, blood volume, and capillary permeability in mammary tumors using two difference contract agents", Journal of Magnetic Resonance Imaging; JMRI, Dec. 2000, vol. 12, No. 6, pp. 991-1003.

* cited by examiner

Primary Examiner — Georgia Y Epps
Assistant Examiner — Magda Cruz
(74) Attorney, Agent, or Firm — Bacon & Thomas, PLLC

(57) ABSTRACT

A method of generating an enhanced perfusion image comprising the use of a blind deconvolution algorithm and the adiabatic approximation to the Johnson and Wilson model (aaJW) and generation of an image, wherein the blind deconvolution algorithm and the aaJW model are used in the generation of values of the following parameters: voxel specific arterial input function $c_p[t]$ and voxel specific tissue residue function $r[t]$.

23 Claims, 6 Drawing Sheets

Anatomical images from perfusion recordings

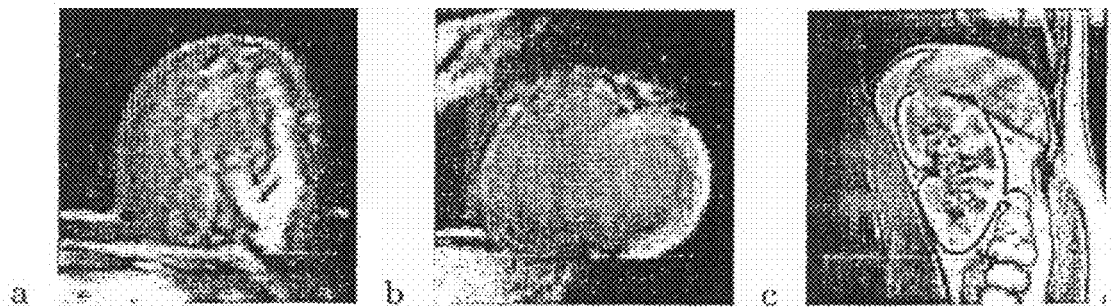
Figure 1: Anatomical images from perfusion recordings
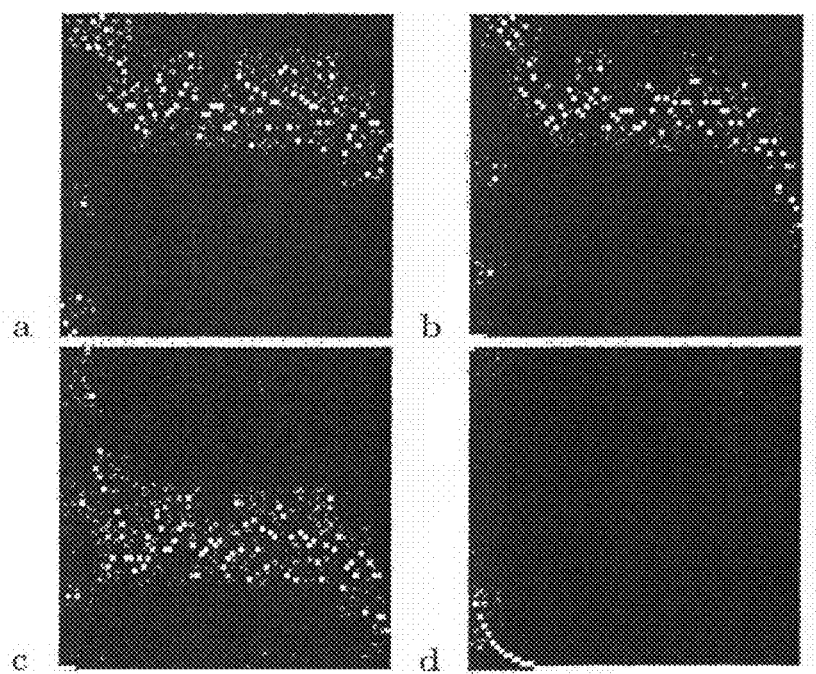
Figure 2: Mammary intraductal carcinoma in situ

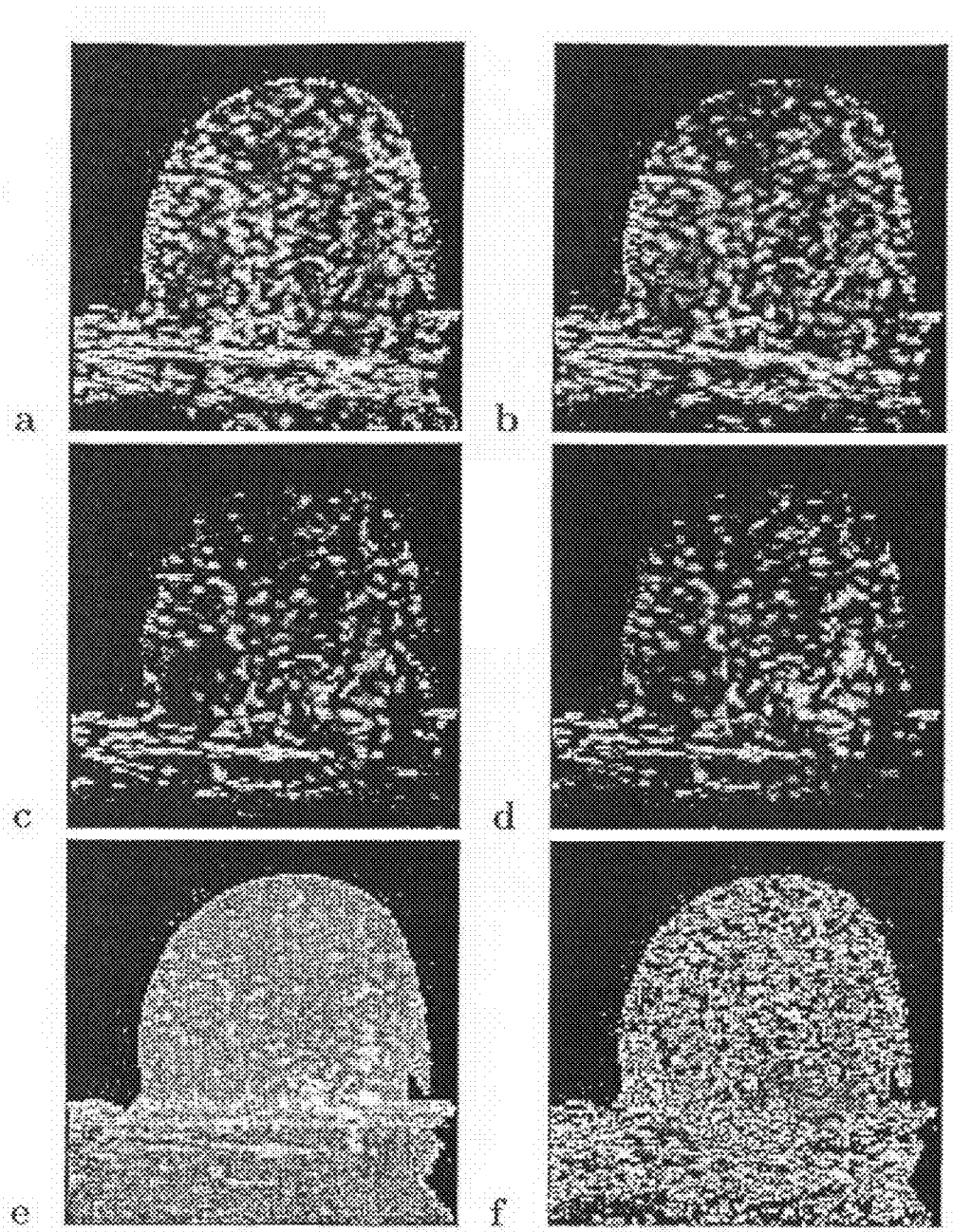
Figure 3: *Mamma with carcinoma in situ in left posterior part*

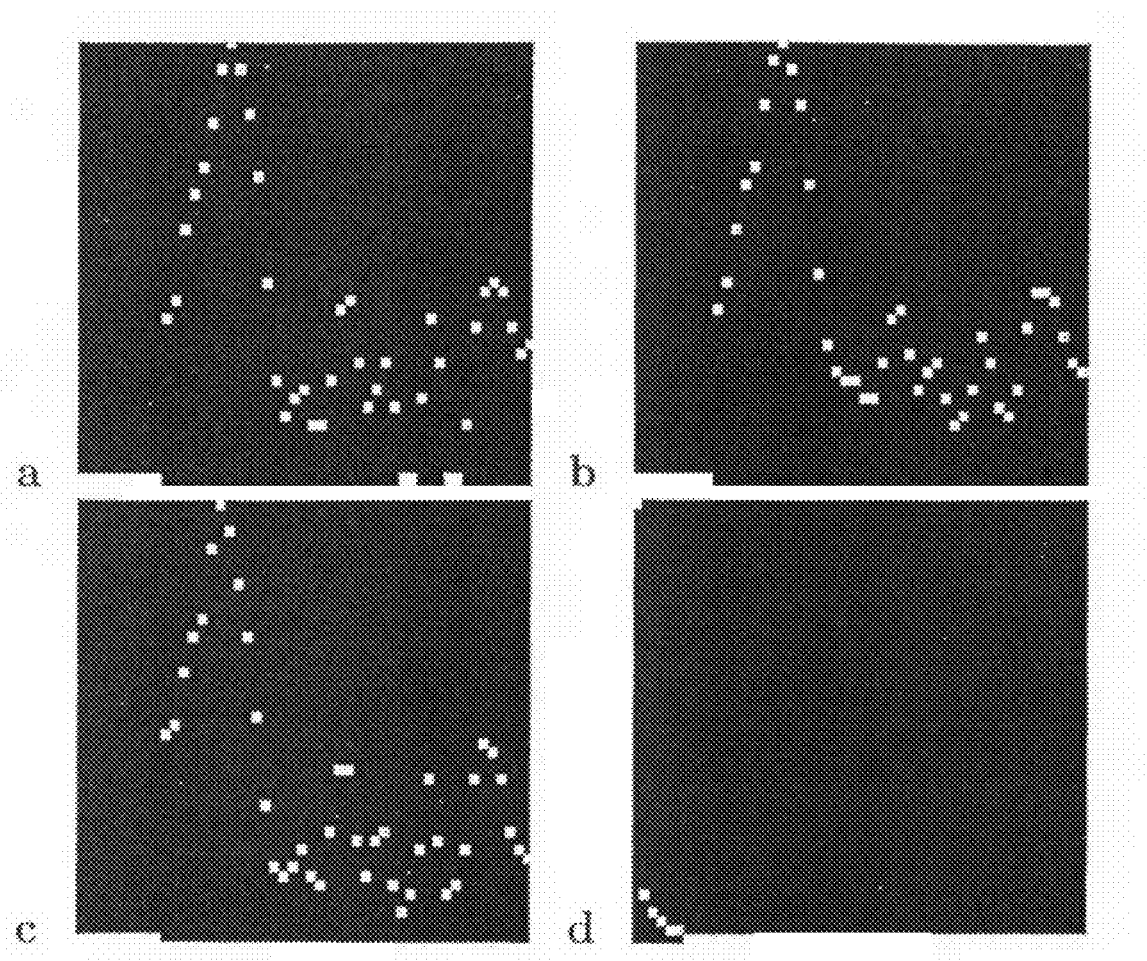
Figure 4: *Heart with old infarct*

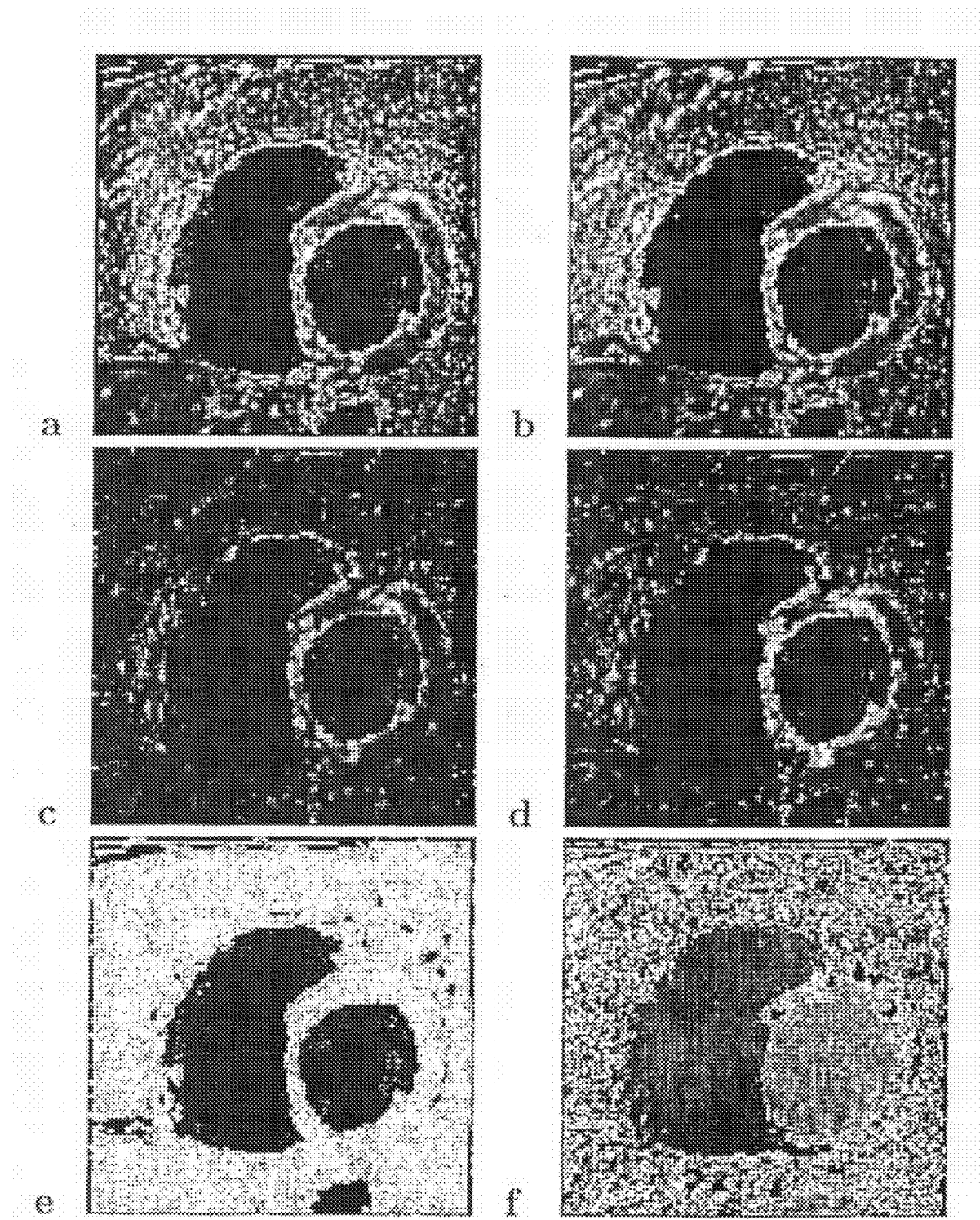
Figure 5: Cardiac left ventricle with a lateral infarct

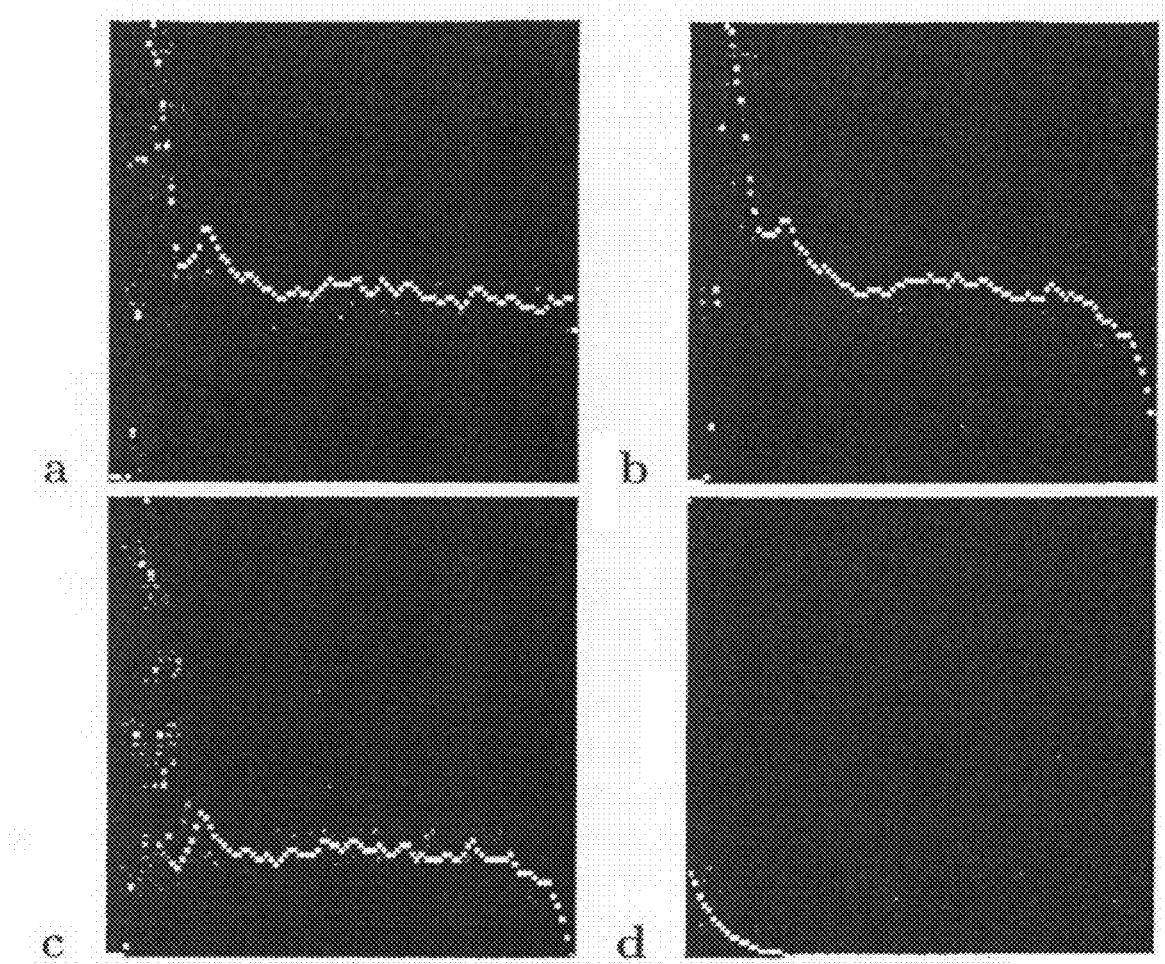
Figure 6: *Normal kidney cortex*

Figure 7: *Normal kidney cortex*

METHOD OF GENERATING AN ENHANCED PERFUSION IMAGE

FIELD OF THE INVENTION

The invention relates to a method of perfusion imaging, as well as to methods of post-imaging data manipulation and programs therefor.

BACKGROUND TO THE INVENTION

Perfusion imaging can be used to detect both physical structure within the body and tissue function and viability. It is particularly useful for studying patients with brain, heart or liver damage, e.g. as a result of stroke, tumours, infarct, etc. Examples of perfusion imaging techniques include Magnetic Resonance Imaging (MRI), Medical ultrasonography (sonography), Positron emission tomography (PET) and Computed Tomography (CT).

In general MRI perfusion techniques, a bolus of a contrast agent (e.g. a gadolinium chelate such as those marketed as Omniscan® or Magnevist® by Amersham and Schering) is administered into the patient's vascular system and images from the region of interest are collected for a period covering the transit of the contrast agent bolus through the tissue in the region of interest. For example, in MRI, fast image acquisition sequences, e.g. spin echo; gradient recall (GRASS or FLASH), echo planar (EPI), RARE, hybrid, half excitation, etc. are used. Such sequences and bolus administration of MR contrast agents for perfusion imaging are well known in the art (see for example "Biomedical Magnetic Resonance Imaging", Ed. Wehrli et al, VCH, 1988).

In clinical practice, it is common for the perfusion image series to be inspected and the results to be assessed qualitatively.

However in many instances a quantified result, e.g. an absolute measurement of regional blood flow, regional blood volume, regional mean transit time, regional time of arrival, regional permeability surface product and regional time to peak are desired (see for example Rempp et al, Radiology 193: 637-641 (1994) and Vonken et al, MRM 41: 343-350 (1999)).

Pharmacokinetic modelling is used to extract voxel specific values for blood plasma flow, blood plasma volume, mean transit time, extravascular extracellular volume, permeability surface area product and time to peak or less physiological perfusion parameters such as the capillary transfer constant, $K_{trans}$. Recirculation of contrast and contrast leakage is included.

The most general pharmacokinetic model introduced so far for MR multi-pass perfusion imaging is the adiabatic approximation model of Johnson and Wilson (aaJW) [Henderson et al. JMRI, Vol. 12: 991-1003 (2000)]. However, the presence of multiple parameters in the aaJW model has made it relatively unstable and highly sensitive to poor signal-to-noise ratio in the underlying data.

The observed tracer perfusion signal of each voxel is a convolution of an unknown voxel specific arterial input function and of an unknown voxel specific tissue residue function (or impulse response function).

The tissue residue function describes the fraction of contrast agent still present in a tissue region at time t and is thus a function dependent on the physiological parameters of the tissue, e.g. blood volume and mean transit time. The arterial input function describes how the contrast agent is delivered to the tissue voxel, and as such gives an impression of the vascular structure in the organ.

With pharmacokinetic modelling, the unknown voxel specific tissue residue function is assumed to have a known parametric form, but with unknown parameter values. The time delay of the tracer arrival and the time to peak of the tracer are specified by the voxel specific arterial input function factor alone. All the remaining perfusion parameters are specified by the flow scaled voxel specific tissue residue function factor.

All known methods using multi-pass pharmacokinetic modelling to find perfusion parameters have problems. For example, the unknown voxel specific arterial input functions may be replaced by a single known arterial input function. This value is generally found by manual or automated identification of voxels inside a vessel. This vessel may be remote from the tissue of interest. Besides, all delay and dispersion of the arterial input function from the vessel used to the tissue of interest are ignored. These modelling simplifications may induce large errors in the estimated perfusion parameters. Ideally, voxel specific arterial input functions should be used to avoid delay and dispersion. In addition, high flow speeds, movements and saturation induce large variability in the arterial input function of major vessels when measured in serial examinations of the same patient.

SUMMARY OF INVENTION

We have now surprisingly found that through a combination of the voxel specific aaJW model and blind deconvolution methods enhanced perfusion imaging is feasible, particularly in the field of magnetic resonance imaging. The use of the method of the present invention also provides significantly more clinically informative values of the arterial input function and tissue residue function.

The method of the present invention also provides high quality physiological parametric images of plasma flow, plasma volume, mean transit time, extraction fraction, permeability surface area product, extravascular extracellular fluid volume and time to peak. These parametric images give direct quantitative estimates of physiological parameters, i.e. the results obtained are physiologically accurate. Such high quality images have not previously been produced and no known single method allows derivation of all of these parametric values. Further, the method of the present invention is not significantly affected by experimental noise.

The estimated voxel specific arterial input functions specify the spatial changes in dispersion and delay of the contrast bolus as it repeatedly passes the imaged area. The tissue residue functions are found without the degrading effects of delay and dispersion introduced by using only a manually identified arterial input function. As a consequence, the estimation scheme for all the vascular parameters becomes linear, simple and noise robust.

Thus viewed from one aspect the invention provides a method of processing perfusion imaging data comprising the use of a blind deconvolution algorithm and the adiabatic approximation model of Johnson and Wilson (aaJW). Preferably, the data is processed on a voxel by voxel basis, i.e. a voxel specific blind deconvolution algorithm and a voxel specific aaJW model are used. Preferably, the data to be processed is recorded at a series of time values [t]. Most preferably, a voxel specific blind deconvolution algorithm and voxel specific aaJW model are applied to perfusion imaging data recorded at a series of time values [t].

A further aspect of the current invention is method of perfusion imaging comprising generating an image of a region of interest of a subject from voxels of said region of interest at a series of time values [t] through the use of a blind deconvolution algorithm and the aaJW model.

A further aspect of the current invention is a method of image processing of a perfusion image comprising the use of a blind deconvolution algorithm and the aaJW model and generation of an image. Preferably, the image is processed on a voxel by voxel basis, i.e. a voxel specific blind deconvolution algorithm and a voxel specific aaJW model are used. Preferably, the perfusion image to be processed comprises a series of data points recorded at a series of time values [t].

In a preferred embodiment of the current invention the blind deconvolution algorithm and the aaJW model are used in the generation of values of the following parameters: voxel specific arterial input function $c_p[t]$ and voxel specific tissue residue function r[t].

In a preferred embodiment of the current invention at least one of the following voxel specific physiological parameters are also determined: plasma flow, plasma volume, mean transit time, extraction fraction, permeability surface area product, extravascular extracellular fluid volume and time to peak.

In a preferred embodiment of the current invention images of at least one or all of the parameters above are produced separately.

In a preferred embodiment of the current invention the blind deconvolution method is used iteratively, particularly preferably the blind deconvolution method is used iteratively to obtain values of the voxel specific arterial input function $c_p[t]$ and the scaled voxel specific tissue residue function u[t].

In a preferred embodiment of the current invention the iterative loop comprises 4 or more iterations, more preferably 6 or more iterations.

In a preferred embodiment of the current invention aaJW is used to generate a voxel specific tissue residue function r[t] from the scaled voxel specific tissue residue function u[t].

In a preferred embodiment of the current invention the initial estimate of the voxel specific arterial input function $c_p[t]$ is the observed voxel specific tracer concentration c[t].

In a preferred embodiment of the current invention the initial estimate of the voxel specific arterial input function $c_p[t]$ is the first pass arterial input function.

In a preferred embodiment of the current invention the initial estimate of scaled voxel specific tissue residue function u[t] is 1.

In a preferred embodiment of the current invention the perfusion imaging method is Magnetic Resonance Imaging (MRI), Medical ultrasonography (sonography), Positron emission tomography (PET) and Computed tomography (CT), most preferably Magnetic Resonance Imaging (MRI).

In a preferred embodiment of the current invention the blind deconvolution method is the Lucy-Richardson deconvolution method or a combination of the Landweber method and Wiener filtering, most preferred is the Lucy-Richardson deconvolution method.

In a preferred embodiment of the current invention a model of the slow water exchange regime is incorporated into the aaJW model.

In a preferred embodiment of the current invention voxel specific values of the average intracellular residence time are generated.

A further aspect of the current invention is an apparatus for use in the method of the current invention, the apparatus having means to receive as an input asset of perfusion imaging signal values for voxels of a region of interest for a series of time values (t), and having means to generate parameters, preferably pharmokinetic parameters therefrom, comprising the use of a blind deconvolution algorithm and the adiabatic approximation model of Johnson and Wilson (aaJW).

A further aspect of the current invention is a computer software product carrying instructions which when executed on a data processing apparatus for use in a method of the current invention will cause the apparatus to be configured to receive as an input a set of perfusion imaging signal values for voxels of a region of interest for a series of time values (t), and to have means to generate values of parameters, preferably pharmokinetic parameters therefrom, comprising the use of a blind deconvolution algorithm and the adiabatic approximation model of Johnson and Wilson (aaJW).

In a yet further aspect of the current invention a method of processing perfusion imaging data to generate the forward ejection fraction comprising the use of a pharmokinetic consensus model and a blind deconvolution algorithm is provided, preferably the forward ejection fraction of the left cardiac ventricle is generated.

DETAILED DESCRIPTION OF INVENTION

The aaJW two compartment model takes into account both capillary transit time and the contribution of the intravascular tracer to the tissue enhancement. In this model, the space in which the tracer is distributed is divided into two cylinders, with tracer exchange between them.

The inner cylinder is the plasma space. The contrast agent concentration Varies with both time and distance along this cylinder. The outer cylinder is the extravascular extracellular space, and is assumed to be a well mixed compartment. Contrast agent concentration in this cylinder varies with time only. Contrast agent may flow between the two compartments, however, the two rate constants for exchange of contrast between plasma and the extravascular extracellular space need not be the same.

Assuming linearity of measurement response and that the blood plasma flow remains constant over the measurement period, the concentration of the tracer in a volume of tissue is:

$$c[t] = F \cdot r[t] * c_p[t] \qquad (1)$$

where the symbol * is the one-dimensional convolution operator, F is plasma flow and t=1, 2, ..., T are the discrete time samples. c[t] is the tissue tracer concentration, $c_p[t]$ is the tracer concentration of arterial plasma and r[t] is the tissue residue function.

The tissue residue function (the impulse response function) for the aaJW model is:

$$r[t] = 1 \qquad 1 \leq t < T_c \qquad (2)$$
$$r[t] = E \cdot e^{\frac{-k_2}{v_e}t} \qquad t \geq T_c$$

where $T_c$ is the mean capillary transit time and $k_2$ is the rate constant for the passage of the tracer from the extravascular extracellular space to intravascular space, $v_e$ is the extravascular extracellular volume per unit volume of tissue (leakage space) and E is the extraction fraction. Using the central volume theorem, $v_p = F \cdot T_c$, where $v_p$ is blood plasma volume per unit volume of tissue.

Several assumptions regarding the mean transport time may be applied to the aaJW model. The mean capillary transit time, $T_c$, may be less than the sampling time of the signal, s[t], then the aaJW model reduces to:

$$r[t] = 1 \quad t = 1 \quad (3)$$
$$r[t] = E \cdot e^{\frac{-k_2}{v_e}t} \quad t > 1$$

$T_c = \Delta s$, where $\Delta s$ is the sampling interval in seconds. Using the central volume theorem again, $v_p = F \cdot \Delta s$ in this case. However, all the information about the tissue dependent variance of $T_c$ is lost.

Ignoring the intravascular plasma volume all together (i.e. $T_c = 0$), $$r[t] = e^{\frac{-k_2}{v_e}t} \quad t \geq 1 \quad (4)$$

However, all information about $v_p$ and $T_c$ is lost. Further assumptions about the perfusion pattern (flow limited, diffusion limited) have to be invoked to estimate plasma flow or the permeability surface area product.

In a preferred embodiment of the current invention, the capillary transfer constant, $K_{trans} = F \cdot E$, is assumed to be the same as $k_2$, the aaJW model residue function for $t \geq Tc$ becomes $$r[t] = 1 \quad 1 \leq t < T_c \quad (5)$$
$$r[t] = E \cdot e^{-\frac{k_{trans}}{v_e}t} \quad t \geq T_c$$

The extraction fraction, E, is the fraction of the tracer that diffuses unidirectionally from plasma into the surrounding tissue during a single tracer transit through the capillary bed. It is related to F and the permeability surface area product PS through $$E = 1 - e^{-PS/F} \quad (6)$$

All these functions and parameters are estimated voxel by voxel. Introducing voxel specific notation, Equation (1) may be written $$c^{i,j}[t] = c_p^{i,j}[t] * F^{i,j} \cdot r^{i,j}[t] = c_p^{i,j}[t] * u^{i,j}[t] \quad (7)$$

where $i = 1, 2, \ldots, I$ and $j = 1, 2, \ldots, J$. I and J are the number of voxels in the x and y-direction, respectively. This form of Equation (7) is used below to find the two factors $c_p^{i,j}[t]$ and $u^{i,j}[t]$ separately through an iterative and blind deconvolution procedure. Thus, for each voxel (i, j), the tracer concentration function of arterial plasma, $c_p^{i,j}[t]$, and the corresponding scaled tissue residue function, $u^{i,j}[t]$, are found.

Since $c_p^{i,j}[t]$ is derived from the tissue tracer concentration function in the voxel of interest, all delay and dispersion caused by the passage of the tracer bolus through the vascular tree to the voxel of interest are included in $c_p^{i,j}[t]$. This is in contrast to using non-voxel specific $c_p[t]$ from an entirely different anatomical location.

The integral $\Omega^{i,j}$, of $c_p^{i,j}[t] = 1, 2, \ldots, T$ which passes through any voxel located completely inside any artery has to be the same for all voxels in a first-pass model, i.e.

$$\Omega = \Omega^{i,j} = \sum_{t=1}^{T} c_p^{i,j}[t],$$

$i = 1, 2, \ldots, I$, $j = 1, 2, \ldots, J$. It follows from Equation (7) that $\Omega$ has to be known to compute $F^{i,j}$ and the other vascular volume perfusion parameters in absolute terms. In contrast, the time dependent parameters, mean transit time, $T_c^{i,j}$ and time to peak, $\tau^{i,j}$, can always be given in absolute values following deconvolution, without knowing $\Omega$. In a preferred embodiment of the current invention, the integral $\Omega$ may be found manually by drawing a region of interest mask inside an artery, another large vessel or inside a heart chamber on the left side, for example. A better estimate may be found by using a pre-bolus injection. Alternatively, the integral $\Omega$ may be found automatically, for example, estimated from applied tracer dose, body weight and body volume using population statistics.

In one embodiment of the current invention, $c_p^{i,j}[t]$ may be scaled completely automatically with respect to the total tracer amount which passes through the voxel of interest by setting $\Omega = \Omega^{i,j} = 1$, $i = 1, 2, \ldots, I$, $j = 1, 2, \ldots, J$. This limited scaling restricts the estimate of $F^{i,j}$, $v_p^{i,j}$ and $v_e^{i,j}$ to relative but not absolute values.

As $c_p^{i,j}[t]$ and $F^{i,j} \cdot r^{i,j}[t]$ are found separately, the estimation of the pharmacokinetic parameters becomes straightforward. There is no delay in $r^{i,j}[t]$, the delay resides in $c_p^{i,j}[t]$. Hence, time to peak for a voxel, $\tau^{i,j}$ is simply the time from a fixed starting point common for all voxels to the maximum point of $c_p^{i,j}[t]$.

In one embodiment of the present invention, the time development of $c_p^{i,j}[t]$ for all voxels at the same time may be displayed in any conventional fashion (e.g. via a video). This allows the regional differences in delay and dispersion of the tracer to be assessed visually.

The parameters $T_c^{i,j}$, $F^{i,j}$ and $K_{trans}^{i,j}$ may be found simultaneously through a least mean square fit procedure of $\log(F^{i,j} \cdot r^{i,j}[t])$. The logarithmic function, log, transforms the last factor of $F^{i,j} \cdot r^{i,j}[t]$ from an expected decaying exponential function to a linear function. This procedure is exemplified with respect to the following preferred example, the logarithm of the relevant part of Equation (5) for the transit time after $T_c$ is taken giving:

$$\log(r^{i,j}[t]) = -k_{ep}^{i,j}t + \log(E) \quad (8)$$

wherein $k_{ep}^{i,j}$ is equal to $k_2^{i,j}/v_e^{i,j}$.

$K_{trans}^{i,j}$ is estimated from $F^{i,j} \cdot E$. If $K_{trans}^{i,j} = k_2^{i,j}$, then also the extravascular extracellular volume fraction, $v_e^{i,j}$ can be estimated.

In the method of the current invention, improved estimates may be found by identifying the first-pass part of $c_p^{i,j}[t]$. A simple search procedure is used to find the first local minimum of $c_p^{i,j}[t]$ after the first-pass maximum point of $c_p^{i,j}[t]$. This local minimum is taken as the upper time limit for the first-pass segment of $c_p^{i,j}[t]$. Then, $v_p^{i,j}$ is simply the time integral of $c_p^{i,j}[t]$ from the starting time point to the local minimum time point.

A preferred embodiment of this procedure is exemplified as follows, based on the configuration of the MR recordings, an estimate of the duration of the first pass pulse can be selected (for example, 25 time samples). The absolute maximum for the voxel specific $c_p^{i,j}[t]$ within these $(25-\Delta A)$ samples is then found, $\Delta$ is usually in the range 2-8. This is at sample time $t_{max}$. Next, the absolute minimum for the voxel specific $c_p^{i,j}[t]$ within the range $[t_{max}, 25]$ is found. This is at sample time $t_{min}$. This minimum is taken as the end of the first, pass pulse in the voxel. Then, the plasma volume is simply the time integral of $c_p^{i,j}[t]$ from $t = 1$ to $t = t_{min}$.

Finally, the central volume theorem can be used to estimate $T_c^{i,j}$ from $T_c^{i,j} = v_p^{i,j}/F^{i,j}$.

Once values of any one of these parameters have been determined parametric images (or "maps") thereof may be produced by any of the standard methods known in the art.

The individual parametric images may be produced separately and automatically, for example, by the apparatus of the current invention. As the current method is significantly unaffected by experimental noise and allows accurate determination of these parameters, the images produced are of a high quality not previously produced in the prior art.

In an embodiment of the current invention the slow water exchange regime may be incorporated into the aaJW model (T. Yankeelev et al, ISMTM conference, Seattle, 2006, Incorporating the effects of transcytolemmal water exchange in the reference region model for DCE-MRI analysis). In this embodiment it is possible to additionally generate voxel specific values of the average intracellular residence time and parametric images thereof. This extension also improves the accuracy of the voxel specific values and parametric maps for the other parameters, in particular when the region of interest is a tumor.

In the method of the current invention blind deconvolution methods are used to separate the arterial input function, $c^{i,j}_p[t]$, and the corresponding scaled tissue residue function, $u^{i,j}[t]$, of each voxel. Preferred blind convolution methods of the present invention comprise the Lucy-Richardson deconvolution method or a combination of the Landweber method and Wiener filtering. In the most preferred embodiment the Lucy-Richardson deconvolution method is applied.

The Lucy-Richardson deconvolution method has several advantages compared to other deconvolution methods when applied to perfusion imaging, particularly MR perfusion imaging. It satisfies the image constraints of positivity, energy conservation and support automatically. Importantly, the inherent positivity constraints for both the arterial input function and the tissue residue function reduce the solution space substantially and thus make the method noise robust.

The Lucy-Robertson deconvolution algorithm works in the spatial domain for images with additive Poisson distributed noise. It is an expectation maximization (EM) algorithm for $u^{i,j}[t]$ and $c^{i,j}_p[t]$ given by $$u^{s+1}[t] = \left\{ \left[ \frac{c[t]}{u^s[t] * c_p^s[t]} \right] * c_p^s[-t] \right\} u^s[t] \quad (9)$$

$$c_p^{s+1}[t] = \left\{ \left[ \frac{c[t]}{u^{s+1}[t] * c_p^s[t]} \right] * u^{s+1}[-t] \right\} c_p^s[t] \quad (10)$$

where s is the iteration number. The indices (i, j), denoting the voxel, have been suppressed. As it is an EM algorithm, it is guaranteed to converge to an optimum, when used alone. The optimum is the maximum posterior probability or likelihood, given the input functions.

Its distance from the global optimum is determined by the initial estimates of the arterial input function. The algorithm may be used twice in an iterative loop. The optimum will usually be local. First, the flow scaled tissue residue function is estimated. Secondly, this new estimate is used to find a new estimate of the arterial input function with the same algorithm. To start the iterations, the initial value of $u^0[t]$ is set constant for the first 40-100 time frames and in later frames to zero. The integral of $u^0[t]$ is set to 1.0. For the arterial input function, $c_p^0[t]=c_t[t]$ for all t.

The vascular parameters of the flow scaled residue function may be estimated after the iterative nonparametric estimation of the two factors of the convolution is complete. However, these parameters may also be estimated right after each iterative update of the scaled residue function. The parameter values are then used to construct an updated parametric estimate of the scaled residue function. This algorithm decreases the log likelihood function more than the nonparametric algorithm; probably through increased noise robustness.

The outer iterative loop may comprise 4 or more iterations, preferably 6 or more iterations. For example, between 4 and 100, preferably between 4 and 10, more preferably between 6 and 10, and most preferably between 6 and 8.

The preferred number of iterations for the two inner loops is one, however, it may be between 1 and 10.

Whilst the methods of the present invention may be used on single- and multi-pass data, multi-pass data is preferably used. By multi-pass it is meant 2 or more passages, e.g. between 2 and 10 passages, of the contrast agent through the tissue of interest The method of the present invention may be used in processing perfusion imaging data to generate the forward ejection fraction comprising the use of a pharmokinetic consensus model and a blind deconvolution algorithm. This is illustrated below.

In an embodiment of the current invention, the tracer concentration function of the left cardiac ventricle can be modelled as a convolution of the multi-pass arterial input function and the left ventricle impulse response for a single well mixed compartment. This impulse response can be interpolated by a monocompartmental exponential model for the forward ejection fraction assessment when the pulse frequency is known. This is equivalent to saying that the pharmacokinetic model of Equation (4) (a pharmokinetic consensus model), is valid inside the ventricle for a monocompartmental exponential model for estimation of the forward ejection fraction.

It follows that inside the left ventricle the double blind deconvolution scheme leads to estimation of the multi-pass left ventricle input function and the left ventricle exponential impulse response function. The only necessary change is to substitute the composite constant $-k_2/v_e$ with a single constant $1/\tau$ Equation (4), giving $$r[t] = E \cdot e^{-\frac{k}{\tau}}, \quad t \geq 1 \quad (11)$$

where t is the sample number. If the pulse interval is $\Delta t$ and the sampling interval is $\Delta s$, the ejection fraction, ef, becomes $$ef = 1 - e^{-\frac{\Delta t}{\tau_1}} \quad (12)$$

where $\tau_1 = \tau \cdot \Delta s$.

Corresponding modelling can be done for the left atrium, which also can be considered a single well mixed compartment. With a peripheral venous injection, the right atrium and right ventricle may not be well mixed.

Any of the blind deconvolution methods described hereinbefore or known in the art may be used in combination with the pharmokinetic consensus model to determine the ejection fraction. A parametric image of the ejection fraction may also be produced as described herein or by any of the methods known in the art.

For performance of the method of the present invention it is only necessary for the values of the parameters used in the algorithms herein to be set in accordance with the characteristics of the imaging device and imaging sequence, and optionally the contrast agent. Appropriate parameter settings may thus be preloaded into the computer program used to perform parametric perfusion image generation such that the operator need only specify to the computer the nature of the contrast agent used. In effect the program supplied by the machine manufacturer may contain a look-up table so that the appropriate values of the parameters needed for the calculation may then be selected automatically. Therefore, high quality individual parametric images of the parameters afforded by the method of the current invention may be easily produced.

Examples of perfusion imaging techniques applicable for use in the method of the current invention include Magnetic Resonance Imaging (MRI), Medical ultrasonography (sonography), Positron emission tomography (PET) and Computed tomography (CT). Particularly preferred is the use of MRI.

If MRI is applied, the use of echoplanar sequences based on spin echo ($T_1$ or $T_2$ imaging) or gradient echo ($T_2$* imaging) signal generation is preferred.

Any conventional techniques known in the state of the art may be combined with the methods of the present invention to improve the quality of the observed data. For example, resolution may be improved by means of zero padding (also known as sinc interpolation and zero filling). Zero padding simply involves appending zeroes to the raw data before the Fourier transform. The application of zero padding avoids the occurrence of wrap around effects of the convolution between the arterial input function and the tissue residue function that otherwise takes place in the Fourier domain.

Edge artifacts in the MR image may be minimised by extrapolating the observed time sequence data set to close to zero by approximating the last part of the observed sequence with a gamma function. Both zero padding and the use of a gamma function are well known methods but are of particular value in combination with the methods described herein.

The methods of the present invention may be applied to both two- and three-dimensional spatial recordings. Three-dimensional data sets may be split up into two-dimensional data sets ("slices") with time as the third dimension. In a preferred embodiment, there is no interaction between the various locations during the calculations, i.e. the calculations for each "slice" and for each voxel are independent of other slices or other voxels.

The skilled person in the art is aware that the necessary sampling rate and the number of time samples are dependent on a series of factors. For example, the nature of the imaging method and the contrast agent used, the degree to which an isolated "bolus" of contrast agent can be administered, and the vascular properties of the tissue of interest all have an impact. Known sampling theorems, such as the Nyquist-Shannon sampling theorem, may be applied to ensure an appropriate sampling rate. Therefore, from knowledge already available in the state of the art, the skilled person would be able to select an appropriate number of time samples taken at an appropriate sampling rate based on region of interest, and the perfusion imaging technique to be used, without undue burden.

In general, a sampling rate of one time sample every 0.1 to 5 seconds may preferably be applied, more preferably a rate of one time sample every 1 to 3 seconds, more preferably every 1.5 to 3 seconds. In general, the higher the sampling rate, the better the resulting estimates, subject to the imaging and processing capabilities of the available equipment.

The number of samples taken may be between 100 and 1000, more preferably between 100 and 500, for example, 150, 200, 300 etc. In general, at a given sampling rate, the slower the vascular properties, the more samples are required. For example, for a tissue with slow vascular tumor properties, 300 samples at a sample rate of 1.5 per second typically gives excellent results for MRI imaging with a gadolinium chelate contrast agent. For a tissue with medium fast vascular properties under similar circumstance, a sampling rate of 1.5 seconds, and 150-200 samples is applicable. These properties can be used as a guide to the necessary parameters for other perfusion imaging techniques. The skilled person will be readily able to select the necessary parameters without undue burden.

In an embodiment of the present invention, the method of the present invention is carried out on a subject pre-administered with a contrast agent, preferably in the form of a bolus. The skilled person will be able to select a suitable known contrast agent based on the method of perfusion imaging applied.

Conventional contrast agents, such as Gd DTPA, Gd DTPA-BMA and Gd HPDO3A which distribute into the extracellular fluid, may be used in the method of the invention to allow estimation of the permeability surface product and extracellular extravascular fluid volume in addition to the other physiological parameters mentioned above. Such agents are well documented in the patent publications of the MR contrast agent manufacturers, e.g. Schering, Amersham, Nycomed, etc.

Blood pooling contrast agents, i.e. those which remain within the vasculature will not allow estimation of the permeability surface product or extracellular extravascular fluid volume because the blood pool agent does not pass through the capillary wall. However, all the other physiological parameters mentioned above can be estimated using blood pool contrast agents (e.g. Vasovist from Schering).

A computer software product for use in implementation of the invention may be provided in the form of a physical carrier such as a disk, tape or other memory device, or may be provided as signals transmitted from a remote location, for example over a network such as the Internet.

The invention will now be described with reference to the following examples and the accompanying drawings in which:

FIG. 1: Anatomical images from perfusion recordings a) Axial section of left mamma with carcinoma in situ in left posterior part. b) Axial section of heart with old infarct in left ventricular wall. c) Coronal section of left normal kidney.

FIG. 2: Mammary intraductal carcinoma in situ Linear scale. Abscissa: 0-1. Ordinate: 0-276 s. a) Mean of the observed tracer concentration in 48 voxel from tumor. b) The estimated tracer concentration of the same voxels. c) The estimated arterial input function of the same voxels. d) The tissue residue function of the same voxels.

FIG. 3: Mamma with carcinoma in situ in left posterior part. a) Plasma flow in ml (window 0-200 ml) per 100 ml of tissue and minute. b) Plasma volume in ml (window 0-15 ml) per 100 ml of tissue. c) Extravascular extracellular fluid volume in ml (window 0-7 ml) per 100 ml of tissue. d) Extraction fraction in ml per ml (window 0-0.4). e) Mean transit time in seconds (range 0-5.4 s). f) Time to peak in seconds (range 0-52 s).

FIG. 4: Heart with old infarct Linear scale. Abscissa: 0-1. Ordinate: 0-65.5 s. a) Mean of the observed tracer concentration in 62 voxel of normal myocardium. b) The estimated tracer concentration of the same voxels. c) The estimated arterial input function of the same voxels. d) The tissue residue function of the same voxels.

FIG. 5: Cardiac left ventricle with a lateral infarct a) Plasma flow in ml (window 0-400 ml) per 100 ml of tissue and minute. b) Plasma volume in ml (window 0-12 ml) per 100 ml of tissue. c) Extravascular extracellular fluid volume in ml (window 0-8 ml) per 100 ml of tissue. d) Extraction fraction in ml per ml (window 0-0.4). e) Mean transit time in seconds (range 0-2.08 s). f) Time to peak in seconds (window 0-20 s).

FIG. 6: Normal kidney cortex Linear scale. Abscissa: 0-1. Ordinate: 0-186 s. a) Mean of the observed tracer concentration in 73 voxel from cortex. b) The estimated tracer concentration of the same voxels. c) The estimated arterial input function of the same voxels. d) The tissue residue function of the same voxels.

FIG. 7: Normal kidney cortex—note that results are invalid for medulla and pelvis. a) Plasma flow in ml (window 0-400 ml) per 100 ml of tissue and minute. b) Plasma volume in ml (window 0-25 ml) per 100 ml of tissue. c) Capillary transfer constant, F·E, (in cortex glomerular filtration rate (GFR)) in ml (range 0-127 ml) per 100 ml of tissue. d) Extraction fraction in ml per ml (window 0-0.4). e) Mean transit time in seconds (window 0-4.0 s). f) Time to peak in seconds (window 7.0-15.0 s).

EXAMPLES

The patient examinations were approved by the regional ethical committee. The breasts of one woman (57 years) with an intraductal carcinoma in situ tumor of the left breast was examined in a prone position with a mamma transmitting coil and a parallel processing (Sense) receiving body coil in a 1.5 Tesla whole body unit (Intera, Philips). The heart of one woman (46 years) with an old heart infarct and the kidneys of one volunteer (54 year man) were examined in the supine position using an 8 channel surface transmitting coil and a parallel processing (Sense) receiving body coil in a 3.0 Tesla whole body unit (GE Signa Excite, Milwaukee, USA). The movement of the breasts during the recording was less than one voxel. No registration was necessary. To minimize misregistration of the heart and kidney images, the pre-contrast image sequences were recorded with complete breath hold at medium inspiration. The post-contrast image sequences were recorded after a few forceful inspirations and expirations at medium inspiration. When needed, the volunteer examined took a few breaths during the recording and continued to hold his breath at medium inspiration. Oxygen (3 litre·min$^{-1}$) was given by a nasal catheter during the whole examination to reduce breathing as much as possible.

Image data were transported to an off line computer for post processing. The procedures were implemented in C, including several Numerical Recipes routines. Image processing tools based on the free XITE package (Dept. of Informatics, University of Oslo, Norway) and MATLAB (Mathworks, Natic, Mass., USA) were used for image handling, visualization and evaluation. To reduce movement artefacts as much as possible, all pre-contrast and post-contrast images of the imaged volume were merged into a single volume image time sequence and registered for translational movement automatically using a maximum likelihood registration algorithm. The maximum translation in both directions in plane was from 10 to 20 voxels. All possible translations for each image volume were tested by brute force, giving computation time, of 12-24 hours on a modern desktop computer.

Images of the heart or kidney where breathing took place were discarded. Corresponding new images without breathing were made by linear interpolation, using the preceding and following volume images. A volume region of interest for the registration was drawn manually.

Following registration, the same Butterworth low-pass filtering was done on each time sequence to reduce out of band noise. The cut-off frequencies were $-\pi/2$ and $\pi/2$ radians and the relative cut-off frequency was 0:3 radians.

Example I

Recordings

Mamma For susceptibility contrast-enhanced perfusion imaging a multisection two-dimensional multishot echoplanar dual echo T2*-weighted (ST1/T2*. PERF) parallel image acquisition sequence was used in the axial plane of the breasts, flip angle $\alpha=40$ degrees, TR=1210 ms, $TE_1=6.0$ ms, $TE_2=30.0$ ms for all sections. The 24 parallel sections had a slice thickness of 5 mm and an in plane voxel size of 1.1×1.1 mm$^2$, corresponding to a voxel volume of 6.05 mm$^3$. The acquisition matrix size had 85 phase encoding steps and 256 frequency encoding steps and the final image matrix was 256×256 pixels. The phase encoding was in the row direction.

To convert the MR signal to tracer concentration and remove $T_1$-effects, no pre-contrast image sequences are necessary with the dual-echo $T_2$*-weighted sequence (see below). After bolus injection of Gd-DTPA (Magnevist) (0.1 mmol/kg) with a power injector (2 ml/s, 7.5 s), followed immediately by a flush of 30 ml saline, the bolus passage was monitored by the next 80 images of each section with the sampling interval 3.63 s.

Heart For relaxivity contrast-enhanced perfusion imaging a $T_1$-weighted inversion recovery gradient echo (SPGR)-parallel image acquisition sequence was used in the axial plane of the heart with TI=10 ms, TR=6:32 ms, TE=1:192 ms for all sections. The 6 parallel sections had a slice thickness of 8 mm, and intersection spacing of 17 mm and an in plane voxel size of 1.25×1.25 mm2, corresponding to a voxel volume of 12.5 mm$^3$. The acquisition matrix size was 128×128 and the image matrix size was 256×256. The field of view was 320×320 mm and the phase encoding was in the row direction.

To be able to convert the MR signal to tracer concentration, three short pre-contrast image sequences of 10 frames each with flip $\alpha=10, 25, 30$ degrees were recorded. After bolus injection of Gadodiamid (Omniscan) (0.1 mmol/kg) with a power injector (4 ml/s, 5 s), followed immediately by a flush of 20 ml saline, the bolus passage was monitored by the next 115 images of each section with the sampling interval 1.71 s and flip angle $\alpha=25$ degrees.

Kidney For relaxivity contrast-enhanced perfusion imaging a $T_1$-weighted LAVA image acquisition sequence was used in the coronal plane with a TR=2:668 ms, TE=1.132 ms for all sections. LAVA is a fast low angle saturation recovery gradient echo sequence with a sense factor of 2 in both in plane directions. The 14 parallel sections had a slice thickness of 5 mm and an in plane voxel size of 1:3672×1:3673 mm$^2$, corresponding to a voxel volume of 9:35 mm$^3$. The acquisition matrix size was 128×128 and the image matrix size was 256×256. The field of view was 350×350 mm. The sampling interval between two consecutive image frames of the same section was 1.856 s. Large pads with manganese sulphate were used between the surface coils and the body to reduce degrading dielectric effects as much as possible.

To be able to convert the MR signal to tracer concentration, four short pre-contrast image sequences of 10 frames each with flip angles $\alpha=4, 8, 12, 15$ degrees were recorded. After bolus injection of a low dose of gadobutrol (Gadovist) (0.01 mmol/kg) with a power injector (3 ml/s, 5 s), followed immediately by a flush of 20 ml saline, the bolus passage was monitored by the next 112 images of each section with the sampling interval 1.856 s and flip angle α=12 degrees.

Example 2

Estimation of Tracer Concentration

To avoid aliasing effects of the tissue residue function in the time domain, it was set to zero for the last 25 time samples of each tracer time sequence. The first three images of each image sequence were discarded to assure steady state signal intensities. A constant relaxivity in blood and tissue and fast transcytolemmal water exchange for the investigated organs were assumed. The relaxivity values of the gadolinium tracers were not necessary for quantification of the vascular parameters. However, the same relaxivity has to be assumed for all tissues during the same examination.

From the tissue relaxivity, the tracer concentration was computed. The relaxivity value of the gadolinium tracer Gadodiamid (Omniscan), at $B_0$=3.0 Telsa is 3.2 $s^{-1}$ $mmol^{-1}$. This gives the tracer concentration $$c^{i,j}[t] = \kappa \cdot (R_1^{i,j}[t] - R_1^{i,j}[0]) \tag{13}$$

where κ is the relaxivity value of the contrast medium at the given strength of the static magnetic field, $B_0$.

Mamma Dual-echo $T_2$*-weighted imaging allows direct quantification of the relaxation rate, $R_2^*[t]=T_2^{*-1}[t]$ without assumptions regarding $T_1$. The recorded signal, s[t] of the echo planar pulse sequence is given by $$s_1[t] = s[0] f(R_1[t]) \cdot e^{-R_2^*[t]TE_m}, m=1, 2 \tag{14}$$

Manipulating Equation (14), it follows that the transverse relaxivity change is, $$\Delta R_2^*[t] = \frac{\ln(S_1[t]/S_2[t]) - \ln(S_{1,pre}/S_{s,pre})}{TE_2 - TE_1} \tag{15}$$

where the subscript pre indicates the corresponding pre-contrast signal. The in plane voxel indices (i, j) have been suppressed for clarity.

Heart The relaxation rate, $R_1[t]=T_1^{-1}[t]$ was calculated for every voxel i,j; i=1, 2 ..., 256, j=1, 2, ..., 256 in each image t; t=1, 2, ..., T from the recorded signal (s) according to equation:

$$s[t] = s[0]\left[(1 - 2e^{-R_1 \cdot TI}) + (1 - E)\frac{1 - a^{n-1}}{1 - a}\right] \tag{16}$$

where a=E cos α, E=$e^{-R_1 \cdot TR}$, α: flip angle and n is the nth phase-encoding line that corresponds to the centre of k-space. Here, only n=1 was used. The in plane indices (i,j) have been suppressed for clarity. TI is the inversion time and TR is the repetition time.

$$s[t] = [0]\frac{1 - e^{-TR \cdot R_1[t]}}{1 - \cos(\alpha)e^{-TR \cdot R_1[t]}} \tag{17}$$

s[0]=con·ρ·sin(α) is a flip angle dependent calibration constant, which includes the receiver gain con and the proton density of the voxel, ρ. The receiver gain con is also voxel specific due to $B_1$ field inhomogeneities and spatially varying receiver sensitivity. The voxel specific con and ρ values were assumed constant during the tracer experiment. Using the estimated voxel specific con values and Equation (16), the relaxation rate, $R_1[t]$, of each voxel was estimated using a linearised version of Equation (16). (Press et al., Numerical Recipes in C).

Kidney The relaxation rate, $R_1[t]=T_1^{-1}[t]$ was calculated for every voxel i, j; i=1, ... 2, ... 256; j=1, 2, ..., 256 in each image t; t=1, 2, ..., T from the recorded signal, s[t] according to the equation:

$$s[t] = s[0]\frac{1 - e^{-TR \cdot R_1[t]}}{1 - \cos(\alpha)e^{-TR \cdot R_1[t]}} \tag{17}$$

where α is the flip angle and the in plane indices (i, j) have been suppressed for clarity. s[0]=con·ρ·sin(α) is a flip angle dependent calibration constant, which includes the receiver gain con and the proton density of the voxel, ρ. The receiver gain con is also voxel specific due to $B_1$ field inhomogeneities and spatially varying receiver sensitivity. The voxel specific con and ρ values were assumed constant during the tracer experiment. The values were estimated using the downhill simplex method in multidimensions of Nelser and Mead.

Arterial Input Function The integral of the arterial input function from voxels with only blood, $c_p[t]$, was estimated by drawing a region of interest inside a large artery in the imaged volume. High flow speeds, movements, saturation and $T_2$* effects induce large variability in the arterial input function of large vessels when measured in serial examinations of the same patient. Hence, a single arterial input function from one section was used for all sections from the same examination. For the mamma and heart recordings, masks were drawn inside the pulmonary artery and left cardiac ventricle, respectively. For the kidney recordings, a mask was drawn inside the lumbar aorta descendens.

Example 3

In Vivo Experiments

To give an overview of the investigated organs, anatomical images were obtained by taking the mean time value of the perfusion series with contrast (FIG. 1 a, c) or without contrast (FIG. 1b).

Mamma with Tumor For the aaJW model, the observed time course of the contrast within a region of interest of the tumor and the convolution of the corresponding estimated arterial input function and tissue residue function overlapped (FIG. 2a, b). The exception was the latest part of the two curves, where the estimated contrast concentration decreased sharply. This decrease was caused by boundary effects of the discrete convolution. The overlap indicates that fairly realistic arterial input functions and tissue residue functions have been found (FIG. 2c, d).

Using the aaJW model, plasma flow and plasma volume (FIG. 3a, b) were not different for normal mamma and in situ carcinoma (Table 1; 1a, 1d). In contrast, transit time (FIG. 3e), extraction fraction (FIG. 3d), permeability surface area product and extravascular extracellular space (FIG. 3c) were clearly lower for the normal mammary tissue than for the in situ carcinoma (Table 1; 1a, 1d). These results fit with the observation that very leaky capillaries are present in mammary carcinomas.

Finally, the time to peak was shorter for the in situ carcinoma than normal mammary tissue (Table 1; 1a, 1d, FIG. 3f). This must mean that the tumor cells have a retrograde effect on the arterial supply.

The consensus model with blind deconvolution gave much lower estimates for plasma flow and plasma volume than the aaJW model. However, the most substantial changes were seen in the mean transit time and the capillary transfer constant (Table 1; 1a, 1b, 1d, 1e). These large differences were probably caused by the approximation errors that may be induced by the simplifications present in the consensus model.

Plasma flow and transit time of the consensus model with and without blind deconvolution differed by a factor of about 2 in opposite direction, while the plasma volumes were similar (Table 1; 1b, 1c). These differences can best be explained by the removal of substantial additional dispersion in the tissue residue function of the blind consensus model. No significant differences were found in the S.D./mean ratio of the delay.

Comparing the vascular parameter values of normal Mamma and carcinoma in situ using the consensus model, there were progressively larger changes in the values (Table 1; 1c, 1f). This is what is to be expected when the carcinoma becomes larger and invades the underlying stromal tissue.

Heart with Infarct Also for the heart using the aaJW model, the observed time course of the contrast within a region of interest of the tumor and the convolution of the corresponding estimated arterial input function and tissue residue function overlapped well (FIG. 4a, b). This observation indicates that fairly realistic arterial input functions and tissue residue functions have been found (FIG. 4c, d).

Using the aaJW model, plasma flow, plasma volume, extraction fraction (FIG. 5a, b, d), permeability surface area product and extravascular extracellular volume (FIG. 5c) were clearly smaller in the old infarct area than in normal myocardium. In contrast, the time to peak was substantially longer in the old infarct area than in normal myocardium (Table 2; 1a, 1d, FIG. 5f). There was no difference in transit time (FIG. 5e). All these changes in vascular parameters agree with the differences in the microvascular properties of normal myocardium and old scar tissue.

The mean transit times were clearly shorter and the corresponding standard deviations smaller for the aaJW model than for the consensus model (Table 2; 1a, 1b, 1d, 1e). These large differences were probably caused by the approximation errors that may be induced by the simplifications present in the consensus model. The mean value of the forward ejection fraction inside a mask of the left ventricle (450 voxels) was 0:21±0:00.

Kidney Cortex For the aaJW model, the observed time course of the contrast within a region of interest of the cortex and the convolution of the corresponding estimated arterial input function and tissue residue function overlapped completely (FIG. 6a, b). Again, this observation indicates that fairly realistic arterial input functions and tissue residue functions have been found (FIG. 6c, d).

Using the aaJW model, the mean glomerular filtration rate was 56 ml/100 ml of tissue/minute (FIG. 6c). Each kidney of adult healthy men weighs about 150 g and the cortex constitutes about 70% of the kidney. Using these values and a tissue density of 1.03 g/ml, the total glomerular filtration rate became 114 ml/min.

The short mean transit time is explained by removal of the additional dispersion of the arterial input functions caused by the passage of blood from the kidney artery to the kidney cortex (FIG. 7e) (Table 3; 1a). The small plasma volume is caused by the use of the central volume therein (Table 3; 1a, FIG. 7b).

The extraction fraction (FIG. 7d) should be less dependent on the deconvolution or parameter estimation method used, since the leakage term and the intravascular plasma fraction term are affected to the same extent by plasma flow and the arterial input function (Equations (1,2)). The kidney cortex permeability surface area product is large (Table 3; 1a, FIG. 7b).

Example 4

Left Cardiac Ventricle Study

The left cardiac ventricles of two volunteers administered with a bolus injection of SonoVue® were examined using a standard GE ultrasound scanner and a standard Philips ultrasound scanner. 4 scans using the GE scanner and 1 scan using the Philips scanner were carried out and the data sets recorded.

The forward ejection fractions for the left cardiac ventricle were calculated from the recorded data sets using blind deconvolution and a pharmokinetic consensus model and also by using the known standard method of delineating the endocardial border in systole and diastole. Using the method of the present invention for calculating the forward ejection fraction, good agreement was obtained for all recordings.

A method for blind deconvolution of voxel specific arterial input functions and tissue residue functions in multi-pass dynamic contrast enhanced perfusion imaging has been presented for the first time. The present invention allows the estimation of vascular parameters became linear, simple and noise robust. The method of the present invention affords the derivation of vascular parameters which are clinically more realistic than those obtained in known methods.

TABLE 1a

Perfusion parameters of mamma.

| Study | Plasma flow | Plasma volume | Transit time | Extr. frac. |
|---|---|---|---|---|
| 1a - Invention | 69 ± 53 | 4 ± 3 | 32.0 ± 0.5 | 0.04 ± 0.06 |
| 1b - Comparative | 20 ± 17 | 4 ± 3 | 10.0 ± 4.8 | — |
| 1c - Comparative | 10 ± 11 | 3 ± 3 | 27.8 ± 15.0 | — |
| 1d - Invention | 172 ± 21 | 5 ± 2 | 4.4 ± 0.1 | 0.26 ± 0.03 |
| 1e - Comparative | 27 ± 8 | 5 ± 2 | 11.6 ± 0.7 | — |
| 1f - Comparative | 14 ± 5 | 5 ± 2 | 22.7 ± 2.7 | — |

Mean ± S.D. Plasma flow in ml/100 ml tissue/min. Plasma volume in ml/100 ml tissue with aaJW model. Study 1b: Results of normal mammary tissue with consensus model. Study 1c: Results of normal mammary tissue with consensus model and known arterial input function. Study 1c: Results of normal mammary tissue with consensus model and known arterial input function. Study 1d: Results of a mammary intraductal carcinoma tumor in situ with aaJW model. Study 1e: Results of a mammary intraductal carcinoma tumor in situ with consensus model. Study 1f: Results of a mammary intraductal carcinoma tumor in situ with consensus model and known arterial input function. The standard deviations in group 1 refers to the variability within 220 voxels of the normal mamma and to the variability within 48 voxels of a mammary intraductal carcinoma tumor in situ. Tissue density assumed equal 1.03 g/ml used in conversion to units given per 100 ml of tissue in group 2, 3, 4 and 6. Plasma flow in group 5 and plasma volume in group 6 estimated by using hematocrit in capillaries = 0.75.

TABLE 1b

Perfusion parameters of mamma -continued.

| Study | PS product | EEV | FE | Time to Peak |
|---|---|---|---|---|
| 1a | 6 ± 9 | 1 ± 2 | 5 ± 9 | 22.9 ± 16.0 |
| 1b | — | 4 ± 6 | 18 ± 16 | 31.2 ± 16.3 |
| 1c | — | 4 ± 4 | 9 ± 10 | 36.3 ± 16.1 |

TABLE 1b-continued

Perfusion parameters of mamma -continued.

| Study | PS product | EEV | FE | Time to Peak |
|---|---|---|---|---|
| 1d | 21 ± 7 | 4 ± 1 | 18 ± 6 | 10.8 ± 4.7 |
| 1e | — | 6 ± 5 | 24 ± 7 | 21.8 ± 2.8 |
| 1f | — | 6 ± 2 | 13 ± 4 | 27.8 ± 7.1 |

Permeability surface area (PS) product in ml/100 ml tissue/min. Extravascular extracellular fluid volume (EEV) in ml/100 ml tissue. FE in ml/100 ml/min tissue. Time to peak in seconds.

TABLE 2a

Perfusion parameters of heart.

| Study | Plasma flow | Plasma volume | Transit time | Extr. frac. |
|---|---|---|---|---|
| 1a - Invention | 129 ± 29 | 4 ± 1 | 1.8 ± 0.1 | 0.18 ± 0.11 |
| 1b - Comparative | 55 ± 21 | 3 ± 1 | 4.0 ± 1.5 | — |
| 1c - Comparative | 77 ± 42 | 3 ± 1 | 3.3 ± 1.4 | — |
| 1d - Invention | 42 ± 17 | 1 ± 0 | 1.7 ± 0.2 | 0.02 ± 0.03 |
| 1e - Comparative | 11 ± 9 | 1 ± 1 | 2.8 ± 0.7 | — |
| 1f - Comparative | 21 ± 18 | 1 ± 1 | 2.2 ± 0.7 | — |

Same units as in Table 1. Study 1a: Present results in normal myocardium of one human heart with infarct in lateral left ventricle wall using the aaJW model. Study 1b: Present results in normal myocardium of one human heart with infarct in lateral left ventricle wall using the consensus model. Study 1c: Present results in normal myocardium of one human heart with infarct in lateral left ventricle wall using the consensus model with known arterial input function. Study 1d: Present results in infarcted myocardium of lateral left ventricle wall in one human heart, using the aaJW model. Study 1e: Present results in infarcted myocardium of lateral left ventricle wall in one human heart, using the consensus model. Study 1f: Present results in infarcted myocardium of lateral left ventricle wall in one human heart, using the consensus model with known arterial input function. The standard deviations in group 1 refers to the variability within 62 voxels of the normal myocardium and to the variability within 85 voxels of a heart with a large infarct. The other standard deviations express variability between patients. Tissue density assumed equal 1.03 g/ml used in conversion to units given per 100 ml of tissue in group 2, 3, 4, 6 and 7. Plasma flow in group 5 and plasma volume in group 6 estimated by using hematocrit in capillaries = 0.75.

TABLE 2b

Perfusion parameters of heart -continued.

| Study | PS product | EEV | FE | Time to Peak |
|---|---|---|---|---|
| 1a - Invention | 28 ± 21 | 2 ± 1 | 24 ± 17 | 9.8 ± 5.1 |
| 1b - Comparative | — | 4 ± 2 | 55 ± 21 | 7.6 ± 5.3 |
| 1c - Comparative | — | 6 ± 4 | 77 ± 42 | 28.5 ± 9.4 |
| 1d - Invention | 1 ± 2 | 0 ± 0 | 1 ± 2 | 17.1 ± 5.3 |
| 1e - Comparative | — | 1 ± 1 | 10 ± 8 | 13.9 ± 6.1 |
| 1f - Comparative | — | 2 ± 1 | 19 ± 16 | 18.5 ± 12.4 |

TABLE 3a

Perfusion parameters of human kidney cortex.

| Study | Plasma flow | Plasma volume | Transit time | Extr. frac. |
|---|---|---|---|---|
| 1a- Invention | 257 ± 65 | 15 ± 3 | 3.6 ± 0.2 | 0.22 ± 0.06 |
| 1b- Comparative | 80 ± 20 | 15 ± 3 | 11.7 ± 1.7 | — |
| 1c- Comparative | 52 ± 13 | 15 ± 4 | 17.3 ± 2.3 | — |

Mean ± S.D. Same units as in Table 1. 73 voxels in cortex mask. Study 1a: Present normal human kidney cortex results with the aaJW model. Study 1b: Present normal human kidney cortex results with the consensus model. Study 1c: Present normal human kidney cortex results with the consensus model with known arterial input function.

TABLE 3b

Perfusion parameters of human kidney cortex -continued.

| Study | PS product | FE (GFR) | Time to Peak |
|---|---|---|---|
| 1a - Invention | 64 ± 22 | 56 ± 18 | 9.0 ± 0.7 |
| 1b - Comparative | — | 80 ± 20 | 7.9 ± 0.9 |
| 1c - Comparative | — | 52 ± 13 | 18.6 ± 23.6 |

Glomerular filtration rate (GFR) in ml/100 ml tissue/min.

The invention claimed is:

1. A method of generating an enhanced perfusion image comprising the use of a blind deconvolution algorithm and the adiabatic approximation to the Johnson and Wilson model (aaJW) and generation of an image, wherein the blind deconvolution algorithm and the aaJW model are used in the generation of values of the following parameters: voxel specific arterial input function $c_p[t]$, and voxel specific tissue residue function $r[t]$.

2. The method of claim 1, further comprising the generation of least one of the following voxel specific parameters: plasma flow, plasma volume, mean transit time, extraction fraction, permeability surface area product, extravascular extracellular fluid volume and time to peak.

3. The method of claim 2, wherein plasma flow, plasma volume, mean transit time, extraction fraction, permeability surface area product, extravascular extracellular fluid volume and time to peak are generated.

4. The method of claim 1, wherein an individual image of any one of said parameters is produced.

5. The method of claim 1, wherein individual images of all parameters recited in claim 1 are produced.

6. The method of claim 1, wherein the blind deconvolution method is used iteratively.

7. The method of claim 6, wherein the blind deconvolution method is used iteratively to obtain values of the voxel specific arterial input function $c_p[t]$ and the scaled voxel specific tissue residue function $u[t]$.

8. The method of claim 7, wherein the iterative loop comprises 4 or more iterations.

9. The method of claim 8, wherein the iterative loop comprises 6 to 10 iterations.

10. The method of claim 7, wherein aaJW is used to generate a voxel specific tissue residue function $r[t]$ from the scaled voxel specific tissue residue function $u[t]$.

11. The method of claim 7, wherein the initial estimate of the voxel specific arterial input function $c_p[t]$ is the observed voxel specific tracer concentration $c[t]$.

12. The method of claim 7, wherein the initial estimate of the voxel specific arterial input function $c_p[t]$ is the integral of the first pass arterial input function.

13. The method of claim 7, wherein the initial estimate of the integral of the scaled voxel specific tissue residue function u[t] is 1.

14. The method of claim 1, wherein the perfusion imaging method is Magnetic Resonance Imaging (MRI), Medical ultrasonography (sonography), Positron emission tomography (PET) and Computed tomography (CT).

15. The method of claim 14, wherein the perfusion imaging method is Magnetic Resonance Imaging (MRI).

16. The method of claim 1, wherein the blind deconvolution method is the Lucy-Richardson deconvolution method or a combination of the Landweber method and Wiener filtering.

17. The method of claim 16, wherein the blind deconvolution method is the Lucy-Richardson deconvolution method.

18. The method of claim 1, wherein a model of the slow water exchange regime is incorporated into the aaJW model.

19. The method of claim 18, wherein voxel specific values of the average intracellular residence time are generated.

20. The method of claim 19, wherein an individual image of the voxel specific average intracellular residence time is produced.

21. The method of claim 1, wherein the perfusion imaging data is multi-pass data.

22. A data processing apparatus for use in the method of claim 1, the apparatus having means to receive as an input a set of perfusion imaging signal values for voxels of a region of interest for a series of time values (t), and having means to generate parameters therefrom comprising the use of a blind deconvolution algorithm and the adiabatic approximation to the Johnson and Wilson model (aaJW).

23. A computer software product carrying instructions which when executed on a data processing apparatus for use in the method of claim 1 will cause the apparatus to be configured to receive as an input a set of perfusion imaging signal values for voxels of a region of interest for a series of time values (t), and to have means to generate values of parameters therefrom comprising the use of a blind deconvolution algorithm and the adiabatic approximation to the Johnson and Wilson model (aaJW).

* * * * *